United States Patent
Koch

(10) Patent No.: US 12,102,521 B1
(45) Date of Patent: Oct. 1, 2024

(54) CRIMPED TEXTILE GRAFT WITH POLYMER LINER

(71) Applicant: Bipore Medical Devices, Inc., Norwood, NJ (US)

(72) Inventor: Durmus Koch, Englewood, NJ (US)

(73) Assignee: Bipore Medical Devices, Inc., Norwood, NJ (US)

( * ) Notice: Subject to any disclaimer, the term of this patent is extended or adjusted under 35 U.S.C. 154(b) by 0 days.

(21) Appl. No.: 18/367,159

(22) Filed: Sep. 12, 2023

Related U.S. Application Data

(60) Provisional application No. 63/472,389, filed on Jun. 12, 2023.

(51) Int. Cl.
*A61F 2/06* (2013.01)
*A61F 2/00* (2006.01)

(52) U.S. Cl.
CPC .............. *A61F 2/06* (2013.01); *A61F 2/0077* (2013.01); *A61F 2210/00* (2013.01)

(58) Field of Classification Search
CPC .... A61L 27/507; A61F 2/06; A61F 2002/072; A61F 2/88; A61F 2/07; A61F 2/0077; A61F 2210/00
See application file for complete search history.

(56) References Cited

U.S. PATENT DOCUMENTS

| | | | |
|---|---|---|---|
| 4,892,539 A | 1/1990 | Koch | |
| 5,897,587 A * | 4/1999 | Martakos | A61F 2/06 623/1.13 |
| 5,911,753 A | 6/1999 | Schmitt | |
| 5,957,974 A * | 9/1999 | Thompson | A61F 2/07 623/1.53 |
| 6,939,377 B2 | 9/2005 | Jayaraman et al. | |
| 7,510,571 B2 | 3/2009 | Spiridigliozzi et al. | |
| 7,879,085 B2 | 2/2011 | Sowinski et al. | |
| 11,589,975 B1 | 2/2023 | Koch | |
| 2003/0139806 A1* | 7/2003 | Haverkost | A61L 27/48 623/1.33 |
| 2004/0182511 A1* | 9/2004 | Rakos | A61F 2/06 156/287 |
| 2007/0073310 A1* | 3/2007 | Pal | A61F 2/07 606/108 |
| 2007/0250153 A1* | 10/2007 | Cully | A61F 2/07 623/1.13 |

(Continued)

FOREIGN PATENT DOCUMENTS

CN 1142974 A * 2/1997 ............. A61L 27/20

OTHER PUBLICATIONS

CN1142974A1_Translation (Year: 1997).*

(Continued)

*Primary Examiner* — Brian A Dukert
*Assistant Examiner* — Rebecca Lynee Zimmerman
(74) *Attorney, Agent, or Firm* — Hoffmann & Baron, LLP

(57) ABSTRACT

A vascular prosthesis includes an outer crimped textile graft and an inner polymeric liner. The polymeric liner is secured to the valleys of the crimps of the textile graft while leaving the peaks of the textile graft free of the liner. The polymeric liner is impermeable to blood flow. The inner liner may include expanded polytetrafluoroethylene polymer, and the graft may include polyethylene terephthalate yarns.

24 Claims, 5 Drawing Sheets

(56) References Cited

U.S. PATENT DOCUMENTS

2016/0250048 A1* 9/2016 Hall ................. A61L 27/18
  623/1.44
2017/0281331 A1* 10/2017 Perkins ................. A61F 2/07

OTHER PUBLICATIONS

Aeos™ ePTFE, Expanded PTFE Products, Biomaterials, ZEUS®, 2 pages, May 24, 2023, https://www.zeusinc.com/products/biomaterials/aeos-eptfe/.
Aeos ™ ePTFE Porous Tubing, Expanded PTFE Porous Tubing, Biomaterials, ZEUS®, 2 pages, May 24, 2023, https://www.zeusinc.com/wp-content/uploads/2022/09/Aeos-Biomaterial-Tubing-V1R1.pdf.
PTFE Polymer, Material Introduction, ZEUS®, 2 pages, May 24, 2023, https://www.zeusinc.com/wp-content/uploads/2023/03/PTFE-Material-V2R2.pdf.

* cited by examiner

CRIMPED TEXTILE GRAFT WITH POLYMER LINER

CROSS-REFERENCE TO RELATED APPLICATIONS

This application claims priority to U.S. Provisional Application No. 63/472,389, filed Jun. 12, 2023, the contents of which is incorporated herein by reference.

FIELD OF THE INVENTION

The present invention is directed to a vascular prosthesis. More particularly, the present invention is directed to a vascular prosthesis having a crimped textile outer surface and a smooth, non-crimped polymeric inner surface.

BACKGROUND OF THE INVENTION

Textile vascular grafts, such as DACRON grafts, are porous or permeable for leakage of a bodily fluid, such as blood. Textile grafts have been coated with animal derived products, such as collagen, to impart fluid impermeability prior to implantation by a practitioner. Textile grafts are often crimped to impart strength, flexibility, non-kinking, etc. properties to the grafts. Such crimped, collagen coated textile grafts, however, do not have smooth inner surfaces that are often desired for smooth flow of blood. Furthermore, about six to seven percent of the population is allergic to collagen, thereby making such textile grafts not suitable for use for the portion of the population.

Some examples of known grafts are described below.

U.S. Pat. No. 4,892,539 discloses crimping of a textile (DACRON) graft by longitudinally compressing the textile graft and heating at an elevated temperature to heat set the crimps. No liner for the textile graft is disclosed.

U.S. Pat. No. 7,879,085 B2 discloses a graft of expanded polytetrafluoroethylene (ePFTE) with a coating of an elastomer. The ePTFE graft is disposed over a shaped mandrel and heating at an elevated temperature to heat set the crimp. No textile graft component is disclosed.

U.S. Pat. No. 5,911,753 discloses a prosthesis with an outer textile graft and a thin inner polytetrafluoroethylene (PTFE) or ePTFE liner having a thickness of 10-50μ. The textile graft included a meltable yarn or a bicomponent yarn having a meltable sheath for securing the textile graft to the liner upon application of heat. No crimping of the textile graft is disclosed.

US 2004/0182511 A1 disclosed a prosthesis of a textile graft and an inner PTFE/ePTFE liner with the having a coating of polycarbonate urethane adhesive. Pressure lamination at elevated temperatures is disclosed to adhesively bond the textile graft and the liner. Only after forming the prosthesis does US 2004/0182511 A1 teach crimping of the prosthesis.

U.S. Pat. No. 6,939,377 B2 discloses a textile graft with an inner polyurethane coating. The graft may further include an optional wire secured to the outside of the textile graft for added support. No crimping of the textile graft is disclosed.

U.S. Pat. No. 7,510,571 B2 discloses a prosthesis having textile graft with a pleated ePTFE liner secured to the textile graft by a polycarbonate urethane adhesive. Only after adhesively joining the textile graft and ePTFE liner is the prosthesis then crimped.

As such, there is a need in the art for crimped textile graft having a smooth, non-crimped polymer liner.

SUMMARY OF THE INVENTION

The present invention is directed to a crimped textile graft having a smooth, non-crimped polymeric liner. Exterior portions and significant interior portions of the crimped graft are free of the polymeric liner to allow for significant tissue ingrowth while still providing for a smooth blood flow.

In one aspect of the present invention, a vascular prosthesis includes:

a tubular graft comprising a tubular textile wall, an inner surface, and outer surface, and opposed first and second open ends, the tubular textile wall having a plurality of crimps defined by a plurality of helical peaks and valleys with crimp wall portions thereinbetween and having biocompatible yarns in a textile construction; and a polymeric tubular member having tubular polymeric wall and opposed first and second open ends, the tubular polymeric wall being substantially impermeable to blood;

wherein the tubular graft is disposed over the polymeric tubular member;

wherein the plurality of valleys of the tubular textile wall are securably disposed to the polymeric tubular member; and wherein the plurality of peaks and the crimp wall portions are substantially free of the polymeric tubular member.

Desirably, the plurality of peaks and the crimp wall portions are disposed away from the polymeric tubular member. Moreover, the plurality of peaks and the crimp wall portions have a spacing away from the polymeric tubular member to define a gap thereinbetween, even though the plurality of valleys of the textile tubular wall are juxtaposingly and directly secured to portions of the polymeric tubular member.

A thermoplastic elastomer may be disposed over portions of the polymeric tubular member proximal to the plurality of valleys of the textile tubular wall to secure the portions of polymeric tubular member to the plurality of valleys of the textile tubular wall. The thermoplastic elastomer may be polyether block amide or polyethylene.

The plurality of peaks and the crimp wall portions disposed away from the polymeric tubular member are desirably free of the thermoplastic elastomer.

Without having thermoplastic elastomer present or the polymer liner securably secured to all portions of the textile graft, the biocompatible yarns at the outer surface are configured to promote the ingrowth of biological tissue thereon. Further, the biocompatible yarns at the inner surface of the plurality of peaks and the crimp wall portions are configured to promote the ingrowth of biological tissue thereon.

The tubular wall of the polymeric tubular member is configured to obviate the leaking of blood at a blood pressure of up to approximately 300 mm Hg. More desirably, the tubular wall of the polymeric tubular member has a water permeability of about 0.16 ml/min/cm$^2$ at 120 mm Hg pressure or less than 0.16 ml/min/cm$^2$ at 120 mm Hg pressure.

Useful biocompatible yarns include polyesters, polypropylenes, polyethylenes, polyurethanes, polytetrafluoroethylenes, and combinations thereof. The biocompatible yarns may be monofilament yarns or multifilament yarns. Desirably, the biocompatible yarns are polyethylene terephthalate yarns. The yarns may be provided in any useful textile construction of the textile graft such as a woven, knitted, or braided textile construction.

The polymeric tubular member is desirably expanded polytetrafluoroethylene. The tubular wall of the polymeric tubular member may have a thickness from about 0.010 inches to about 0.030 inches. Moreover, the tubular wall of the polymeric tubular member may have a porosity from about 70 percent to about 90 percent. The tubular wall of the polymeric tubular member may have a density from about 0.22 g/cm$^3$ to about 0.65 g/cm$^3$.

The vascular prosthesis may further include an elongate metallic member disposed at the inner surface of the textile tubular wall proximal to the peaks and distal from the polymeric tubular member. The metallic member may be an elongate ribbon or an elongate wire. The metallic member may have a thickness from about 0.002 inches to about 0.004 inches. The metallic member may include a metallic material, such as stainless steel, nickel titanium alloy, cobalt-based alloy, platinum, gold, titanium, tantalum, niobium and combinations thereof. Desirably, the metallic member includes nickel titanium alloy.

Thus, the present invention provides a significant improvement over the current state of textile grafts by providing a vascular prosthesis having a crimped textile outer prosthesis surface configured to promote the ingrowth of biological tissue thereat, including into portions of the crimps themselves, while providing a smooth, non-crimped inner polymeric prosthesis surface.

These and other features and advantages of the present invention will become apparent from the following detailed description of illustrative embodiments thereof, which is to be read in connection with the accompanying drawings. Corresponding reference element numbers or characters indicate corresponding parts throughout the several views of the drawings.

BRIEF DESCRIPTION OF THE DRAWINGS

FIGS. 8-12 schematically illustrate a non-limiting method for preparing the vascular prosthesis of FIG. 1, in which:

FIG. 8 schematically illustrates a cylindrical mandrel useful in accordance with the present invention, FIG. 9 schematically illustrates the placement of the polymeric tubular liner over the mandrel of FIG. 8, FIG. 10 schematically illustrates the placement of a thermoplastic elastomer over the polymeric tubular liner of FIG. 9 in a desirable ribbon-like pattern, FIG. 11 schematically illustrates the placement of the crimped tubular textile graft over the mandrel and components of FIG. 10, and FIG. 12 schematically illustrates the placement of a tie down wire or ribbon over the crimped tubular textile graft of FIG. 10.

DETAILED DESCRIPTION OF THE INVENTION

Figure 1:
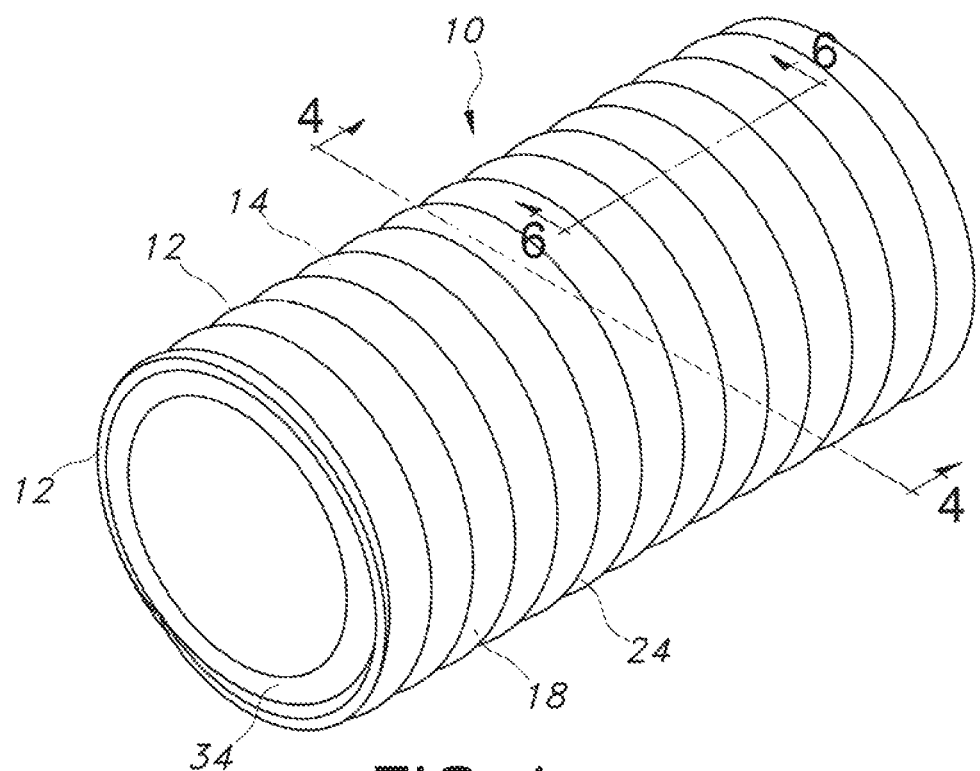
FIG. 1 is a perspective view of a vascular prosthesis of the present invention having an outer crimped tubular textile graft and an inner polymeric tubular liner.

FIG. 1 is a perspective view of the vascular prosthesis 10 of the present invention. The vascular prosthesis 10 includes an outer textile graft 12 and an inner polymeric member 34. The tubular graft 12 includes a textile tubular wall 14 having an outer surface 18. The textile tubular graft 12 includes a plurality of crimps 24.

Figure 2:
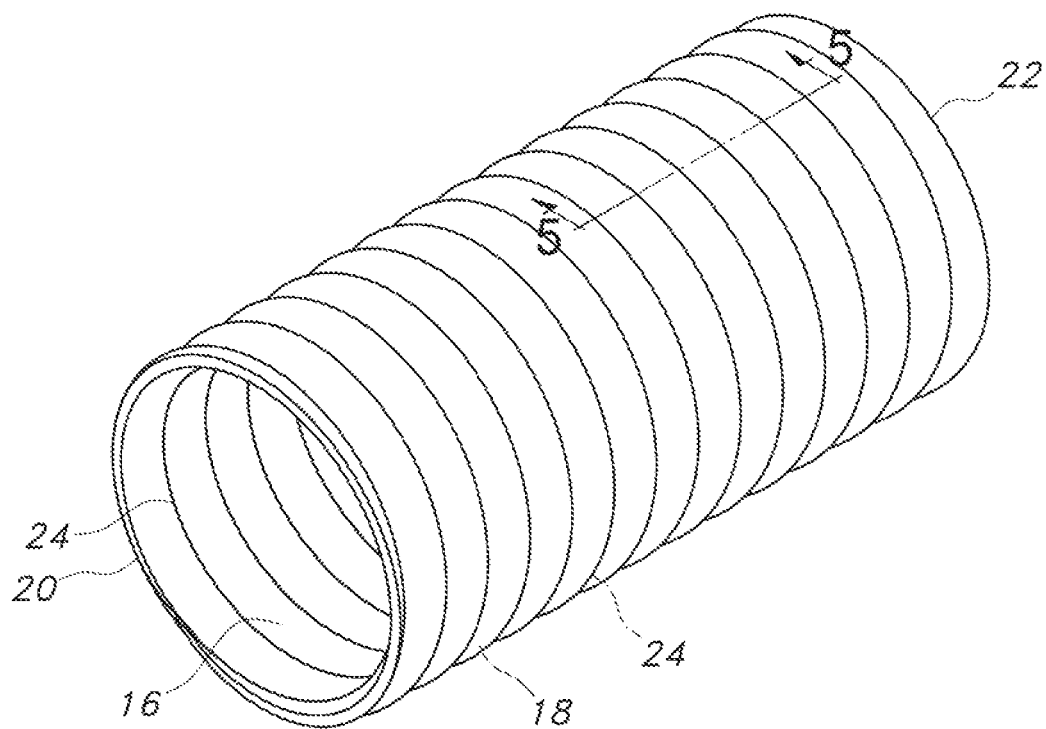
FIG. 2 is a perspective view of the crimped tubular textile graft of FIG. 1.

FIG. 2 is a perspective view of the textile graft 12 of the vascular prosthesis 10 of the present invention. The textile graft 12 includes a first open end 20 and an opposed second open end 22. As depicted in FIG. 2, both the outer surface 18 of the textile graft 12 and the inner surface 16 of the textile graft 12 includes crimps 24.

The textile wall 14 of the tubular graft 12 and the vascular prosthesis 10 may include wall portions made from any biocompatible, durable material, including, for example polyesters, such as polyethylene terephthalate (PET); naphthalene dicarboxylate derivatives, such as polyethylene naphthalate, polybutylene naphthalate, polytrimethylene naphthalate, trimethylenediol naphthalate; polytetrafluoroethylenes (PTFE); expanded polytetrafluoroethylene (ePTFE); polyurethanes; polyamides; polyimides; polycarbonates; natural silk; polyethylene; polypropylene; and combinations thereof. As used herein, textile materials are filaments or yarns that are woven, braided, knitted, filament-spun, and the like to form textile graft material. Desirably, the textile wall 14 of the tubular graft 12 is a woven poly(ethylene terephthalate) or woven PET textile tubular member.

The nominal diameter (D) of the vascular prosthesis 10 may vary according to the intended use. For example, the vascular prosthesis 10 may be a small diameter graft having a nominal diameter (D) of less that about 6 mm, for example from about 2 mm to about 6 mm. Further, the vascular prosthesis 10 may be a large diameter graft having a nominal diameter (D) of about 6 mm to 24 mm, including about 6 mm, about 7 mm, about 8 mm, about 10 mm, about 12 mm, about 14 mm, about 16 mm, about 18 mm, about 20 mm, about 22 mm, and about 24 mm.

Figure 3:
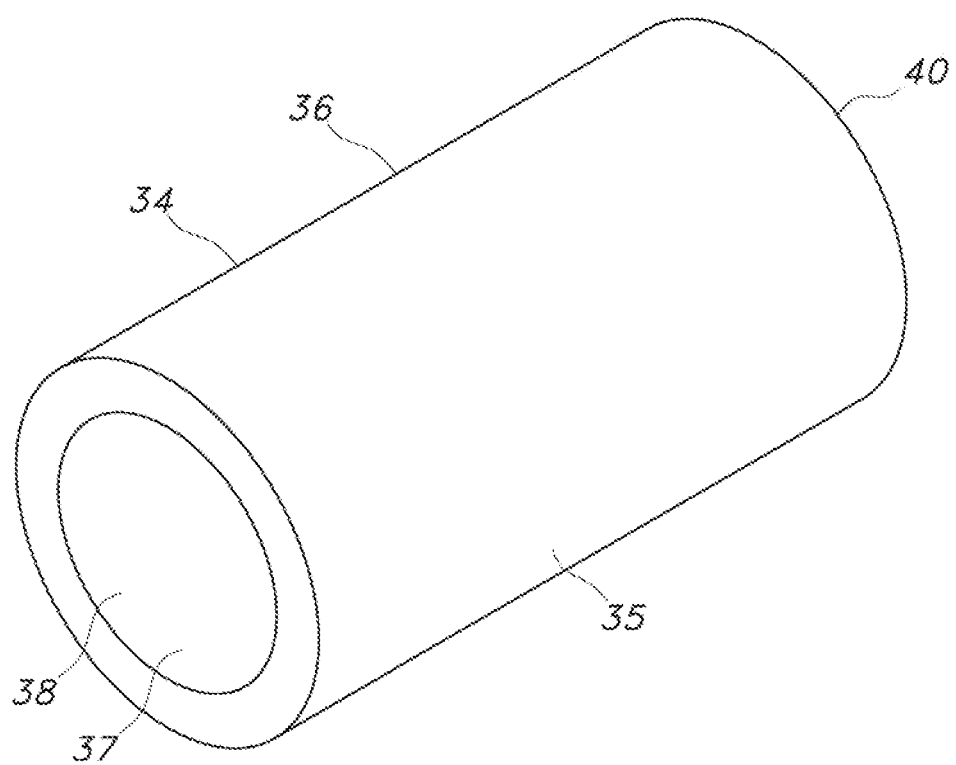
FIG. 3 is a perspective view of the inner polymeric tubular liner of FIG. 1.

FIG. 3 is a perspective view of the tubular polymeric member 34 of the vascular prosthesis 10 of the present invention. The tubular polymeric member 34 includes a first open end 38 and an opposed open end 40 with a polymeric wall 36 thereinbetween. Both the outer surface 35 and the inner surface 37 of the polymeric wall 36 are substantially smooth, e.g., substantially free of crimps, folds, pleats, seams, and the like. Moreover, the polymeric wall 36 is free of holes or open lattice patterns that would thwart the desired impermeability of the polymeric wall 36.

The polymeric wall 36 or the tubular polymeric member 34 may include expanded polytetrafluoroethylene (ePTFE). Expanded PTFE (ePTFE) tubes may be made by extrusion of PTFE resin, typically mixed with a lubricant. Desirably, ePTFE includes a microporous structure of ePTFE may be obtained by a process that involves rapid stretching of the extruded tube at high temperature. The ePTFE structure or the polymeric wall 36 may be characterized by small nodes, typically about 5 to 10 µm (or micrometers) wide by 5 to 100 µm long, interconnected by fibrils of less than about 0.5 µm in diameter. The degree of porosity of an ePTFE graft is controlled, in part, by the distance between the nodes (e.g., internodal distance or IND). Internodal distances from about 10 µm to about 100 µm are useful for the polymeric wall 36 with the present invention. Desirably, the internodal distance of the ePTFE is from about 20 µm to about 60 µm. More desirably, the internodal distance of the ePTFE is from about 30 µm to about 45 µm. Node and fibril dimensions, including internodal distances, may be obtained through scanning electron microscope (SEM) techniques and analysis.

The density of the ePTFE for the polymeric wall 36 may be from about 0.22 g/cm$^3$ to about 1.52 g/cm$^3$, more desirably from about 0.22 g/cm$^3$ to about 1.09 g/cm$^3$. A density from about 0.22 g/cm$^3$ to about 0.65 g/cm$^3$ is also useful with the present invention for the polymeric wall 36.

The porosity of the ePTFE for the polymeric wall 36 may be from about 30 percent to about 90 percent, more desirably from about 50 percent to about 90 percent. A porosity from about 70 percent to about 90 percent is also useful with the present invention for the polymeric wall 36.

Porosity or porosity measurements may be obtained various methods. One useful method includes providing a know size of an ePTFE sample, such as a rectangular sample, measuring the length, width, thickness, and mass of the sample to determine the bulk density of the sample. Percent porosity is then obtained by subtracting the measured bulk density of the sample and that of the bulk density of PTFE used to produce the ePTFE from 1 and then multiplying by 100. Bulk density of PTFE is typically from about 2.16 g/cm$^3$ to about 2.22 g/cm$^3$.

The polymeric wall 36 may have a non-limiting thickness from about 0.010 inches (about 250 µm) to about 0.030 inches (about 750 µm). Desirably, the thickness may be from about 0.010 inches (about 250 µm) to about 0.020 inches (about 500 µm). More desirably, the thickness may be from about 0.015 inches (about 380 µm) to about 0.020 inches (about 500 µm). A thickness of about 0.015 inches (about 380 µm) is also desirable.

Figure 4:
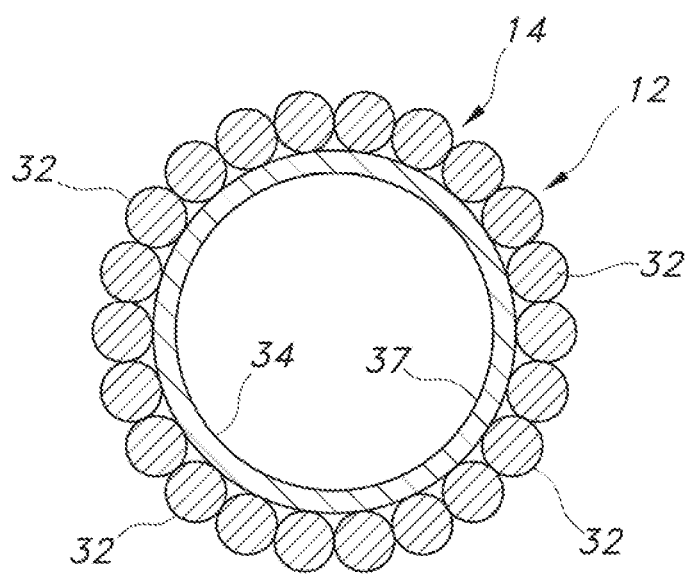
FIG. 4 is a cross sectional view of the vascular prosthesis of FIG. 1 taken along the 4-4 axis.

FIG. 4 is a cross-sectional view of the vascular prosthesis 10 taken along the 4-4 axis in FIG. 1. The textile wall 14 of the tubular graft 12 includes a plurality of biocompatible yarns 32. The yarns 32 are depicted in FIG. 4 as being juxtaposingly disposed over the polymeric tubular member 34. As described further below, such juxtaposingly disposed yarns represent the low portions or valleys of the crimps 24 of the tubular graft 12.

The yarns 32 may include yarns of any of the above described biocompatible material described in conjunction with the textile wall 14. The yarns 32 may be of the monofilament, multifilament, or spun type. The yarns 32 may have a linear density from about 18 denier (about 20 decitex) to about 140 denier (about 154 decitex). The yarns 32 may be flat, twisted, and/or textured, and may have high, low or moderate shrinkage and/or bulk and crimp properties. Twisted yarns include S-twisted yarns and Z-twisted yarns.

The textile wall 14 of the tubular graft 12 may be woven from yarns 32 using any known weave pattern, including simple plain weaves, basket weaves, twill weaves, velour weaves and the like. Weave patterns include warp yarns running along the longitudinal length of the woven product and weft also known as fill yarns running around the width or circumference of the woven product. The warp and the fill yarns are at approximately 90 degrees to one another with fabric flowing from the machine in the warp direction.

Knitting involves the interlooping or stitching of yarn into vertical columns (wales) and horizontal rows (courses) of loops to form the knitted fabric structure. In warp knitting, the loops are formed along the textile length, i.e., in the wale or warp direction of the textile. Useful knitting patterns include, but are not limited to, locknit knits (also referred to as tricot or jersey knits), reverse locknit knits, sharkskin knits, queenscord knits, atlas knits, velour knits, and the like.

Figure 5:
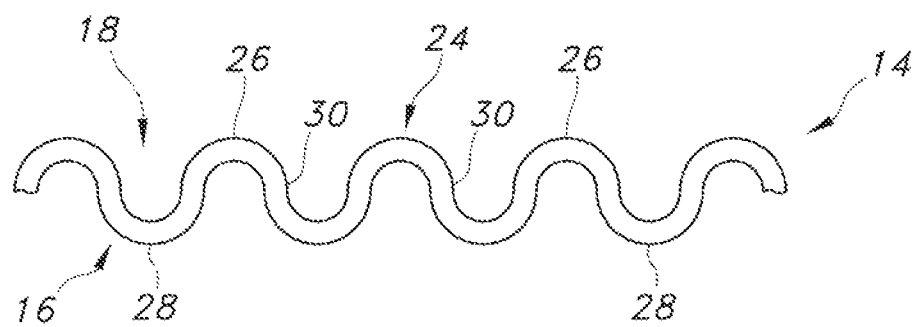
FIG. 5 is a partial cross sectional view of the textile graft of FIG. 2 taken along the 5-5 axis.

FIG. 5 is a cross-sectional view of a portion of the tubular textile wall 14 of the tubular textile graft 12 taken along the 5-5 axis of FIG. 2 showing the crimps 24 of the wall 14. The crimps 24 include a plurality of upper or raised portions or peaks 26 and a plurality of lower portions or valleys 28. Between the peaks 26 and the valleys 28 of the textile wall 14 are crimp wall portions 30. As depicted in FIG. 5 the outer surface 18 of the tubular graft 12 is characterized by, for example, the peaks 26, and the inner surface 16 of the tubular graft 12 is characterized by, for example, the valleys 28.

Figure 6:
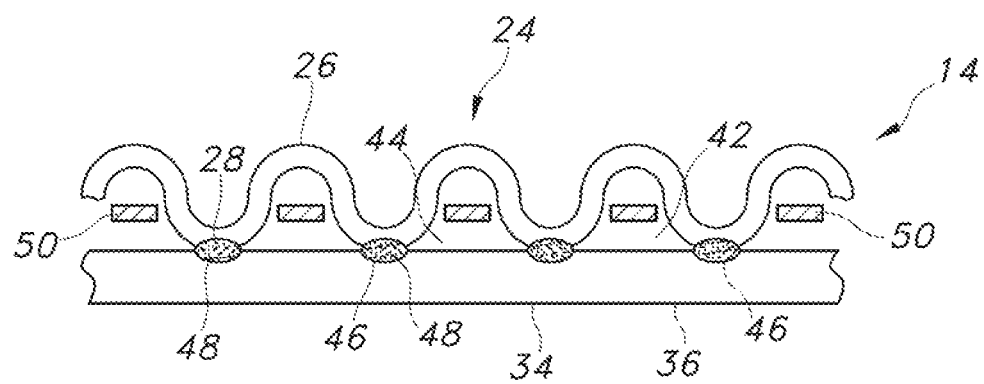
FIG. 6 a partial cross sectional view of the vascular prosthesis of FIG. 1 taken along the 6-6 axis.

FIG. 6 is a cross-sectional view of a portion of the vascular prosthesis 10 taken along the 6-6 axis of FIG. 1. The valleys 28 are securably disposed to portions 46 of the polymeric tubular member 34. A thermoplastic elastomer 48 is used to secure the valleys 28 to the portions 46 of the polymeric tubular member 34. As the textile tubular wall 14 is porous, the thermoplastic elastomer 48 permeates or impregnates the yarns 32 of the textile tubular wall 14. As described above, the polymeric tubular wall 36 includes ePTFE and a microporous structure of nodes and fibrils with a high degree of porosity over bulk PTFE. As such, the thermoplastic elastomer 48 permeates or impregnates the pores of the ePTFE to securably dispose the valleys 28 to the portions 46 of the polymeric tubular member 34.

The thermoplastic elastomer 48 any useful biocompatible thermoplastic or adhesive materials, such as polyether block amide (PEBAX) or polyethylene (PE), or use of adhesives such as polycarbonate-urethane or fluorinated ethylene propylene (FEP). These materials are non-limiting, and other suitable biocompatible thermoplastic elastomeric materials may be used.

As depicted in FIG. 6, the thermoplastic elastomer 48 is not disposed towards or at the peaks 26 or at significant crimp wall portions 30 between the peaks 26 and valleys 28. Thus, the peaks 26 and the crimp wall portions 30 are free, including substantially free, of the thermoplastic elastomer 48. Further, as depicted in FIG. 6, the peaks 26 and the crimp wall portions 30 are free, including substantially free, of polymeric tubular member 34, including any significant portions of the polymeric wall 36 of polymeric tubular member 34. As such there is a spacing 42 and gap 44 between the outer surface 18, including the peaks 26 and associated crimp wall portions 30, of the textile tubular wall 14 and the polymeric tubular member 34. Thus, the outer surface 18, including the peaks 26 and associated crimp wall portions 30, of the textile tubular wall 14 is configured to promote the ingrowth of biological tissue thereon after implantation. Further, the polymeric wall 36 of polymeric tubular member 34 is sufficiently robust or thick to also mitigate portions of the polymeric 36 from being juxtaposingly disposed towards the e peaks 26 and associated crimp wall portions 30 of the textile tubular wall 14

Figure 7:
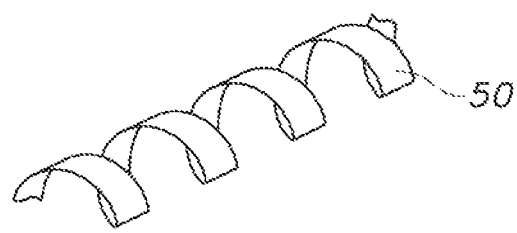
FIG. 7 is a perspective view of coiled metallic member useful for providing additional strength or support of the textile prosthesis of the present invention.

As depicted in FIGS. 6 and 7, the vascular prosthesis 10 may include an elongate metallic member 50. The elongate metallic member 50 may be in the form of a spiral or coil as depicted in FIG. 7. The elongate metallic member 50 is useful for, especially in smaller diameter vascular prostheses, for example vascular prostheses having a non-limiting nominal diameter of about 4 mm to about 6 mm, providing reinforcement, if needed, to the prosthesis. The metallic member 50 is desirably an elongate ribbon or an elongate wire. The ribbon and/or wire may have a thickness or diameter from about 0.002 inches (about 50 μm) to about 0.004 inches (about 100 μm), including a thickness or diameter of about 0.003 inches (about 75 μm). The width of the ribbon may be from about 0.003 inches (about 75 μm) to about 0.030 inches (about 750 μm), depending upon the size of the graft and its crimps.

The elongate metallic member 50 may be made from a flexible, metallic material. One useful metallic material is nickel-titanium alloy (NiTi), such as NITINOL. Other materials such as, but not limited to, stainless steel, cobalt-based alloy such as ELGILOY, titanium, tantalum, niobium and combinations thereof. Desirably, the elongate metallic member 50 is a shape memory material, such as nickel-titanium alloy or NITINOL. Such shape memory material may be heat set into a desired shape, such as the coiled tubular shape described above, by placing the shape memory material into the desired shape and annealing at elevated temperatures, such as 550° C. to 550° C., followed by cooling and quenching. The heat setting conditions are non-limiting and other conditions may suitably be used.

With the use of the polymeric tubular member 34, the vascular prosthesis 10 may be a fluid tight implantable prosthesis which configured to obviate the leaking of blood at a blood pressure of up to approximately 300 mmHg. There is no need for preclotting with collagen or the like as the inner polymeric tubular member 34 is generally blood impermeable. Such a fluid tight implantable prosthesis may have a water permeability of less that about 5 ml/min/cm$^2$ at 120 mm Hg pressure, more desirably less than about 1 ml/min/cm$^2$ at 120 mm Hg pressure, preferably about 0.16 ml/min/cm$^2$ at 120 mm Hg pressure or less than 0.16 ml/min/cm$^2$ at 120 mm Hg pressure. The use of the inner polymeric tubular member 34 also offers other benefits. For example, ePTFE layers also prevent or inhibit or minimize undesirable adhesion or build-up of materials, such as thrombus formation, platelet aggregation, and the like.

Figure 8:
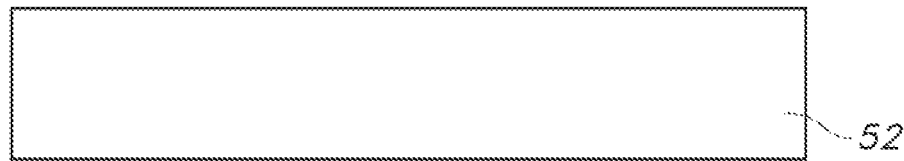

FIGS. 8-12 schematically depict a method for forming the vascular prosthesis 10 of the present invention. As depicted in FIG. 8, a mandrel 52 is provided. The mandrel 52 is typically a cylindrical mandrel, but other shaped mandrels may be suitable used. For example, if the vascular prosthesis 10 is tapered, flared, flanged etc., the mandrel 52 may be correspondingly shaped. The mandrel 52 may be made from any useful material, such as but not limited to stainless steel. Desirably, the mandrel 52 has a smooth outer surface.

Figure 9:
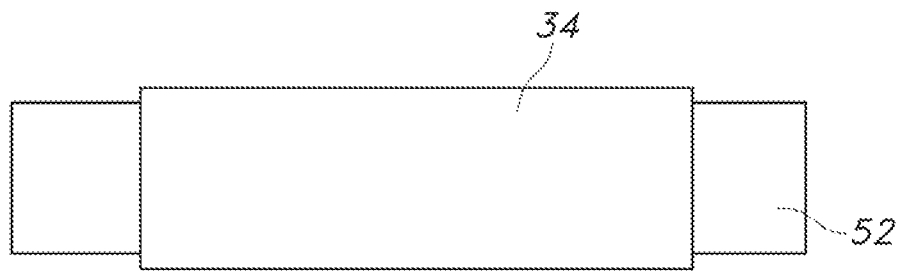

As depicted in FIG. 9, the polymeric tubular member 34 is disposed over the mandrel 52 by any suitable means. For example, the polymeric tubular member 34 may be slidably disposed over the mandrel 52.

Figure 10:
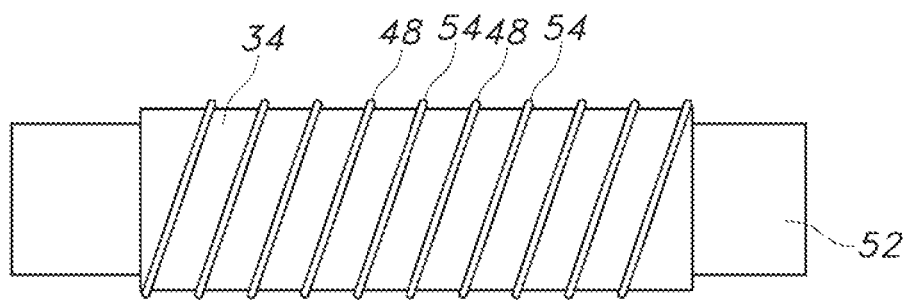
Figure 11:
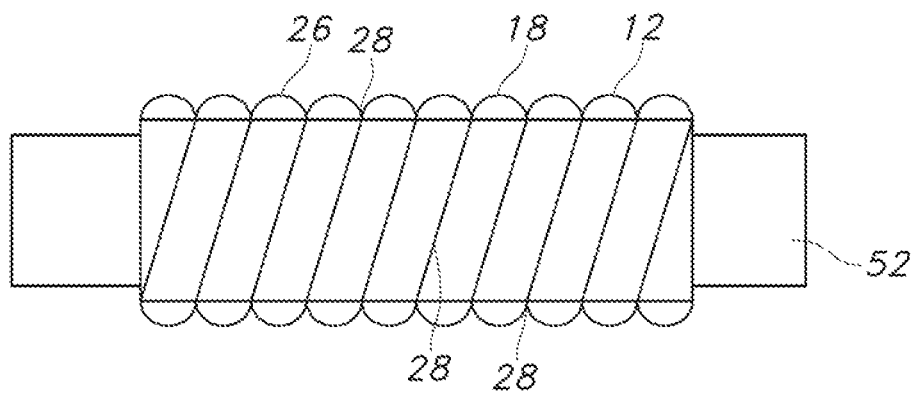
Figure 12:
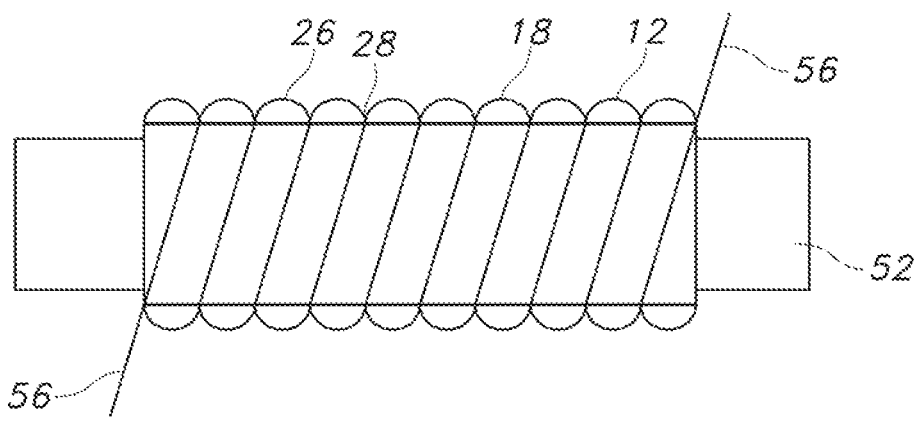

As depicted in FIG. 10, the thermoplastic elastomer 48 is disposed in a pattern 54. The pattern 54 may be in the form of a ribbon or thread of material, including a helical pattern, either continuous or substantially continuous. The pattern 54 may approximate the crimp pattern of the textile graft 12. As depicted in FIG. 11, the crimped textile graft 12 is disposed over the polymeric tubular member 34 and the pattern 54 of the thermoplastic elastomer 48. The textile graft 12 is disposed over the mandrel 50 such that the valleys 28 are juxtaposingly disposed over the thermoplastic elastomer 48, including the pattern 54 thereof. As depicted in FIG. 12, an elongate tie down member 56 may be wrapped, including helically wrapped, about the textile graft 12. Desirably, the elongate member 56 is laid down or disposed substantially on the valleys 28 of the crimps 24. The elongate member 56 may be of any suitable shape, for example a (round) wire, thread, ribbon, and the like.

The elongate tie down member 56 may be a metallic wire, suitable for applying pressure to the underlying vascular prosthesis 10 and for conducting heat. The assembly of FIG. 12 may then be subjected to thermal energy or heated, in for example an oven. The temperature should be sufficient to at least partially melt or induce flow of the thermoplastic elastomer 48 into the pores of the polymeric tubular member 34, such as ePTFE pores, and into the textile wall 14 at the valleys 28. The use of a conductive metallic wire for the elongate member 56 facilitates localized heating or localized application of thermal energy for bonding of the thermoplastic elastomer 48. The temperature should be sufficient to melt or induce flow of the thermoplastic elastomer 48 while not damaging the textile graft 12 and the polymeric tubular member 34. Such temperatures may be suitably chosen by one skilled n the art. For example, PE and PEBAX have low melting points of about 100° C. and 170° C., respectively, as compared to high melting points of about 260° C. and 327° C. for PET and PTFE, respectively.

The elongate member 56 may any suitable metallic material, including metals having high thermal conductivity such as copper (about 400 W/m° K) and aluminum (about 240 W/m° K) and including metals having low or moderate thermal conductivity, for example less that about 100 W/m° K, such as nickel-titanium, stainless steel (about 15 W/m° K), cobalt-based, titanium (about 15 W/m° K), tantalum (about 55 W/m° K), and niobium. These materials are non-limiting and other suitable materials, including other metals and even non-metallic materials may be used. For example, polymeric materials having low thermal conductivity properties (<1 W/m° K), such as nylon.

Thermal heat need not be applied by use of an oven, and other heating techniques may be suitably used. For example, localized thermal energy may be applied by focused or localized radiating, conductive, and/or convective means. Such focused or localized thermal energy may be especially useful when the elongate member 56 is a polymeric material of low thermal conductivity.

The present invention, however, is not limited to a vascular prosthesis 10 having the elongate metallic member 50. For example, the vascular prosthesis 10 of the present invention is kink-resistant, including substantially non-kinking, even without the use of the elongate metallic member 50. This kink resistance is present in both small diameter vascular and large diameter vascular grafts. While not being bound to any particular theory, it is believed that having just the valleys 28 of the tubular graft 12 secured to the polymeric tubular member 34 provides the kink resistance by providing support to the tubular graft 12 and by restricting movement of the crimps 24.

Figure 13:
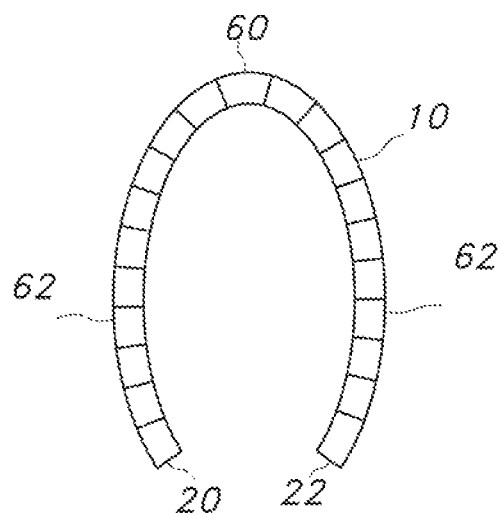
FIG. 13 schematically illustrates non-kinking characteristics of the vascular prosthesis of the present invention.
Figure 14:
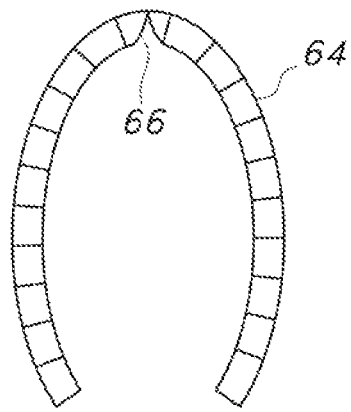
FIG. 14 schematically illustrates kinking of vascular graft according to the prior art.

For example, as depicted in FIG. 13, the vascular prosthesis 10 may be bent about 180 degrees, i.e., one end 20 moved about 90 degrees and the other end 22 also moved about 90 degrees, without any kinking. As such, the vertex 60 of the bent vascular prosthesis 10 maintains the substantially tubular or circular shape as with the other portions 62 of the vascular prosthesis 10. The degree of bending without substantially kinking is not limited to 180 degree bends. For example, the vascular prosthesis 10 can be looped, i.e., 360 degree bend or greater, without kinking. In contrast, as depicted in FIG. 14, a prior art textile graft 64 without having internal metallic supports or stents or without having polymeric monofilament reinforcing coils typically kink, as shown at kink 66 when bents to any significant degree including 180 degree bend.

While various embodiments of the present invention are specifically illustrated and/or described herein, it will be appreciated that modifications and variations of the present invention may be effected by those skilled in the art without departing from the spirit and intended scope of the invention. Further, any of the embodiments or aspects of the invention as described in the claims or in the specification may be used with one and another without limitation.

Element reference numbers, letters, and/or symbols in the following embodiments or aspects of the present invention are presented merely for ease of comprehension and are not to be construed as limiting the scope of the present invention. Further, the following embodiments or aspects of the invention may be combined in any fashion and combination and be within the scope of the present invention, as follows:

Embodiment 1. A vascular prosthesis (10) comprising:
- a tubular graft (12) comprising a tubular textile wall (14), an inner surface (16), and outer surface (18), and opposed first and second open ends (20, 22), the tubular textile wall (14) having a plurality of crimps (24) defined by a plurality of helical peaks (26) and valleys (28) with crimp wall portions (30) therein between and having biocompatible yarns (32) in a textile construction; and
- a polymeric tubular member (34) having tubular polymeric wall (36) and opposed first and second open ends (38, 40), the tubular polymeric wall (36) being substantially impermeable to blood;
- wherein the tubular graft (12) is disposed over the polymeric tubular member (34);
- wherein the plurality of valleys (28) of the tubular textile wall (14) are securely disposed to the polymeric tubular member (34); and
- wherein the plurality of peaks (26) and the crimp wall portions (30) are substantially free of the polymeric tubular member (34).

Embodiment 2. The vascular prosthesis (10) of embodiment 1, wherein the plurality of peaks (26) and the crimp wall portions (30) are disposed away from the polymeric tubular member (34).

Embodiment 3. The vascular prosthesis (10) of embodiment 1 or any previous embodiments, wherein the plurality of peaks (26) and the crimp wall portions (30) have a spacing (42) away from the polymeric tubular member (34) to define a gap (44) therein between.

Embodiment 4. The vascular prosthesis (10) of embodiment 1 or any previous embodiments, wherein the plurality of valleys (28) of the textile tubular wall (14) are juxtaposingly and directly secured to portions (46) of the polymeric tubular member (34).

Embodiment 5. The vascular prosthesis (10) of embodiment 1 or any previous embodiments, further comprising a thermoplastic elastomer (48) disposed over portions (46) of the polymeric tubular member (34) proximal to the plurality of valleys (28) of the textile tubular wall (14) to secure the portions (46) of polymeric tubular member (34) to the plurality of valleys (28) of the textile tubular wall (14).

Embodiment 6. The vascular prosthesis (10) of embodiment 5 or any previous embodiments, wherein the thermoplastic elastomer (48) is polyether block amide or polyethylene.

Embodiment 7. The vascular prosthesis (10) of embodiment 5 or any previous embodiments, wherein the plurality of peaks (26) and the crimp wall portions (30) disposed away from the polymeric tubular member (34) are free of the thermoplastic elastomer (48).

Embodiment 8. The vascular prosthesis (10) of embodiment 1 or any previous embodiments, wherein the biocompatible yarns (32) at the outer surface (18) of the textile tubular wall (14) are configured to promote the ingrowth of biological tissue thereon.

Embodiment 9. The vascular prosthesis (10) of embodiment 1 or any previous embodiments, wherein the biocompatible yarns (32) at the inner surface (16) of the plurality of peaks (26) and the crimp wall portions (30) are configured to promote the ingrowth of biological tissue thereon.

Embodiment 10. The vascular prosthesis (10) of embodiment 1 or any previous embodiments, wherein the tubular wall (36) of the polymeric tubular member (34) is configured to obviate the leaking of blood at a blood pressure of up to approximately 300 mmHg.

Embodiment 11. The vascular prosthesis (10) of embodiment 1 or any previous embodiments, wherein the tubular wall of (36) the polymeric tubular member (34) has a water permeability of about 0.16 ml/min/cm$^2$ at 120 mm Hg pressure or less than 0.16 ml/min/cm$^2$ at 120 mm Hg pressure.

Embodiment 12. The vascular prosthesis (10) of embodiment 1 or any previous embodiments, wherein the biocompatible yarns (32) are selected from the group consisting of polyesters, polypropylenes, polyethylenes, polyurethanes, polytetrafluoroethylenes, and combinations thereof.

Embodiment 13. The vascular prosthesis (10) of embodiment 1 or any previous embodiments, wherein the biocompatible yarns (32) are monofilament yarns or multifilament yarns.

Embodiment 14. The vascular prosthesis (10) of embodiment 1 or any previous embodiments, wherein the biocompatible yarns (32) are polyethylene terephthalate yarns.

Embodiment 15. The vascular prosthesis (10) of embodiment 1 or any previous embodiments, wherein the textile construction is a woven, knitted, or braided textile construction.

Embodiment 16. The vascular prosthesis (10) of embodiment 1 or any previous embodiments, wherein the polymeric tubular member (34) comprises expanded polytetrafluoroethylene.

Embodiment 17. The vascular prosthesis (10) of embodiment 16 or any previous embodiments, wherein the tubular wall of (36) the polymeric tubular member (34) has a thickness from about 0.010 inches (about 250 micrometers) to about 0.030 inches (about 750 micrometers).

Embodiment 18. The vascular prosthesis (10) of embodiment 16 or any previous embodiments, wherein the tubular wall of (36) the polymeric tubular member (34) has a porosity from about 70 percent to about 90 percent.

Embodiment 19. The vascular prosthesis (10) of embodiment 16 or any previous embodiments, wherein the tubular wall of (36) the polymeric tubular member (34) has a density from about 0.22 g/cm$^3$ to about 0.65 g/cm$^3$.

Embodiment 20. The vascular prosthesis (10) of embodiment 1 or any previous embodiments, further comprising an elongate metallic member (50) disposed at the inner surface (16) of the textile tubular wall (14) proximal to the peaks (26) and distal from the polymeric tubular member (34).

Embodiment 21. The vascular prosthesis (10) of embodiment 20 or any previous embodiments, wherein the metallic member (50) has a thickness from about 0.002 inches (about 50 micrometers) to about 0.004 inches (about 100 micrometers).

Embodiment 22. The vascular prosthesis (10) of embodiment 20 or any previous embodiments, wherein the metallic member (50) is an elongate ribbon or an elongate wire.

Embodiment 23. The vascular prosthesis (10) of embodiment 20 or any previous embodiments, wherein the metallic member (50) comprises a metallic material selected from the group consisting of from stainless steel, nickel titanium alloy, cobalt-based alloy, platinum, gold, titanium, tantalum, niobium and combinations thereof.

Embodiment 24. The vascular prosthesis (10) of embodiment 20 or any previous embodiments, wherein the metallic member (50) comprises nickel titanium alloy.

What is claimed is:

1. A vascular prosthesis comprising:
    a tubular graft comprising a tubular textile wall, an inner surface, and outer surface, and opposed first and second open ends, the tubular textile wall having a plurality of crimps defined by a plurality of helical peaks and valleys with crimp wall portions thereinbetween and having biocompatible yarns in a textile construction;
    a polymeric tubular member having tubular polymeric wall and opposed first and second open ends, the tubular polymeric wall being substantially impermeable to blood; and
    a thermoplastic elastomer disposed over portions of the polymeric tubular member proximal to the plurality of valleys of the textile tubular wall to secure the portions of polymeric tubular member to the plurality of valleys of the textile tubular wall;
    wherein the tubular graft is disposed over the polymeric tubular member;
    wherein the plurality of valleys of the tubular textile wall are securably disposed to the polymeric tubular member;
    wherein the plurality of peaks and the crimp wall portions are substantially free of the polymeric tubular member;
    wherein the biocompatible yarns at the inner surface of the plurality of peaks and the crimp wall portions are configured to promote the ingrowth of biological tissue thereon; and
    wherein the plurality of peaks and the crimp wall portions disposed away from the polymeric tubular member are free of the thermoplastic elastomer.

2. The vascular prosthesis of claim 1, wherein the plurality of peaks and the crimp wall portions are disposed away from the polymeric tubular member.

3. The vascular prosthesis of claim 1, wherein the plurality of peaks and the crimp wall portions have a spacing away from the polymeric tubular member to define a gap thereinbetween.

4. The vascular prosthesis of claim 1, wherein the plurality of valleys of the textile tubular wall are juxtaposingly and directly secured to portions of the polymeric tubular member.

5. The vascular prosthesis of claim 1, wherein the thermoplastic elastomer is polyether block amide or polyethylene.

6. The vascular prosthesis of claim 1, wherein the biocompatible yarns at the outer surface are configured to promote the ingrowth of biological tissue thereon.

7. The vascular prosthesis of claim 1, wherein the tubular wall of the polymeric tubular member is configured to obviate the leaking of blood at a blood pressure of up to approximately 300 mmHg.

8. The vascular prosthesis of claim 1, wherein the tubular wall of the polymeric tubular member has a water permeability of about 0.16 ml/min/cm$^2$ at 120 mm Hg pressure or less than 0.16 ml/min/cm$^2$ at 120 mm Hg pressure.

9. The vascular prosthesis of claim 1, wherein the biocompatible yarns are selected from the group consisting of polyesters, polypropylenes, polyethylenes, polyurethanes, polytetrafluoroethylenes, and combinations thereof.

10. The vascular prosthesis of claim 1, wherein the biocompatible yarns are monofilament yarns or multifilament yarns.

11. The vascular prosthesis of claim 1, wherein the biocompatible yarns are polyethylene terephthalate yarns.

12. The vascular prosthesis of claim 1, wherein the textile construction is a woven, knitted, or braided textile construction.

13. The vascular prosthesis of claim 1, wherein the polymeric tubular member comprises expanded polytetrafluoroethylene.

14. The vascular prosthesis of claim 13, wherein the tubular wall of the polymeric tubular member has a thickness from about 0.010 inches to about 0.030 inches.

15. The vascular prosthesis of claim 13, wherein the tubular wall of the polymeric tubular member has a porosity from about 70 percent to about 90 percent.

16. The vascular prosthesis of claim 13, wherein the tubular wall of the polymeric tubular member has a density from about 0.22 g/cm$^3$ to about 0.65 g/cm$^3$.

17. The vascular prosthesis of claim 1, further comprising an elongate metallic member disposed at the inner surface of the textile tubular wall proximal to the peaks and distal from the polymeric tubular member.

18. The vascular prosthesis of claim 17, wherein the metallic member has a thickness from about 0.002 inches to about 0.004 inches.

19. The vascular prosthesis of claim 17, wherein the metallic member is an elongate ribbon or an elongate wire.

20. The vascular prosthesis of claim 17, wherein the metallic member comprises a metallic material selected from the group consisting of stainless steel, nickel titanium alloy, cobalt-based alloy, platinum, gold, titanium, tantalum, niobium and combinations thereof.

21. The vascular prosthesis of claim 17, wherein the metallic member comprises nickel titanium alloy.

22. A vascular prosthesis comprising:
    a tubular graft comprising a tubular textile wall, an inner surface, and outer surface, and opposed first and second open ends, the tubular textile wall having a plurality of crimps defined by a plurality of helical peaks and valleys with crimp wall portions thereinbetween and having biocompatible yarns in a textile construction; and
    a polymeric tubular member having tubular polymeric wall and opposed first and second open ends, the tubular polymeric wall being substantially impermeable to blood;
    wherein the tubular graft is disposed over the polymeric tubular member;
    wherein the plurality of valleys of the tubular textile wall are securably disposed to the polymeric tubular member;
    wherein the plurality of peaks and the crimp wall portions are substantially free of the polymeric tubular member; and
    wherein the biocompatible yarns at the inner surface of the plurality of peaks and the crimp wall portions are configured to promote the ingrowth of biological tissue thereon.

23. The vascular prosthesis of claim 22, further comprising a thermoplastic elastomer disposed over portions of the polymeric tubular member proximal to the plurality of valleys of the textile tubular wall to secure the portions of polymeric tubular member to the plurality of valleys of the textile tubular wall.

24. The vascular prosthesis of claim 23, wherein the plurality of peaks and the crimp wall portions disposed away from the polymeric tubular member are free of the thermoplastic elastomer.

* * * * *